United States Patent [19]

Hope

[11] Plant 4,567

[45] Jul. 8, 1980

[54] KALANCHOE NAMED PRINCESS

[75] Inventor: Claude Hope, Cartago, Costa Rica

[73] Assignee: Pan-American Plant Company, West Chicago, Ill.

[21] Appl. No.: 10,416

[22] Filed: Feb. 8, 1979

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new cultivar of kalanchoe characterized by its bright pink florets which range from 12 to 14 mm. in diameter, an extended blooming period due to continuous flower bud development over several weeks, a uniform 10-week flowering response for year around flowering with photoperiod control, and its medium plant height with medium sized glossy foliage.

1 Drawing Figure

BACKGROUND OF THE NEW PLANT

This new variety of kalanchoe plant originated as a seedling of unidentified parentage growing in my breeding facilities at Cartago, Costa Rica, and identified in my records as Seedling #57-12. This new plant was discovered by me in 1970 and because of its abundant production of bright pink florets, it was selected for propagation and trial which was done by me, by means of cuttings from the original plant, at Cartago, Costa Rico. Propagation of this new plant through successive generations by vegetative cuttings has shown that its distinctive characteristics hold true from generation to generation and appear to be firmly fixed. Commercial production of this new plant by vegetative cuttings is now being carried on at Parrish, Fla., and at West Chicago, Ill.

DESCRIPTION OF THE DRAWING

My new kalanchoe plant is illustrated by the accompanying photographic drawing which shows the growth and flower display characteristics of the plant, as well as the flower color, the colors shown being as nearly true as it is reasonably possible to obtain by conventional full-color photographic procedures.

DESCRIPTION OF THE NEW PLANT

The following is a detailed description of my new variety of kalanchoe plant with color designations according to The R.H.S. Colour Chart published by The Royal Horticultural Society of London, England, in collaboration with The British Colour Council.

THE PLANT

Origin: Seedling.
Parentage: Unidentified.
Classification:
*Botanic.*—*Kalanchoe blossfeldiana.*
*Commercial.*—Flowering kalanchoe pot plant.
Form: Bush.
Height: 19 to 24 cm.
Growth: Sturdy and upright with good strength and medium vigor.
Branching: Normal under natural conditions.
Foliage:
*Size of leaf.*—Length — about 4.7 to 10.0 cm. Width — about 2.6 to 8.8 cm.

*Shape of leaf.*—Elliptical, with dentate margins.
*Surface texture.*—Thick and smooth with a fleshy tip of obtuse form.
*Color.*—Upper side — 147A, 147B. Under side — 138B.
*Venation.*—Pinnate.
*Petioles.*—Length — about 0.7 to 2.4 cm.

THE BUD

Size:
*Diameter.*—About 2.0 to 2.5 mm.
*Depth.*—About 9 to 11 mm.
Opening rate: Rapid; bud opens fully within one day.
Sepals: 4 or 5, surrounding the receptacle.
*Form.*—Upstanding and spear-shaped.
*Surface texture.*—Smooth.
Aspect.—Shiny.
*Color.*—Inside — 144A. Outside — 144A.

THE FLOWER

Recommended flowering: Year around with photoperiod control.
Response: 10-week.
Natural flowering season: November through January under Costa Rican environment.
Blooms: Flower type — regular and complete.
*Borne.*—On a compound cyme.
*Size.*—Small — about 12 to 14 mm. in diameter and 9 to 11 mm. in depth.
*Shape.*—When the bloom first opens, the shape is generally flat; as the bloom matures, the petals reflex.
*Petals.*—Normally each flower has 4 petals and occasionally, less than 5%, the flower will have 5 petals. Form: Separate and distinct; nearly oval in shape. Texture: Firm. Appearance: Shiny. Color:

| | Young | Mature | Old |
|---|---|---|---|
| Upper side: | 43D | 58B–58C | 61D |
| Under side: | 52D | 55C | 55C–55D |

*Tonality of florescence at a distance of* 6 *feet.*—58-B–58C.
*Discoloration.*—Moderate fade after full bloom.
*Peduncle.*—Upright and sturdy with smooth surface texture. Color: 146C and 199A.

Persistence: Flowers hang on and dry.

Effect of weather: None. Recommended for greenhouse culture only.

Disease resistance: This plant has been observed to resist powdery mildew in environments where that disease is present.

Fragrance: Typical kalanchoe.

Lasting quality: Approximately 4 weeks on plant.

REPRODUCTIVE ORGANS

Stamens: Number — 8 to 10.

*Anthers.*—Color — yellow.

*Filaments.*—Color — yellow-green.

*Pollen.*—Color — yellow.

Pistils: Number — 4 or 5.

*Stigmas.*—Color — initially yellow-green, turning to off-white as flower ages.

Ovaries: 4 or 5 in number each developing multiple seeds.

My new kalanchoe plant is particularly characterized by its bright pink florets which exhibit only moderate fading as the blooms become aged, its uniform 10-week flowering response under photoperiod control and its extended blooming period which results from a continuous flower bud development during the first few weeks of blooming. This plant can be flowered the year around. It grows rapidly, reaching a medium plant height when flowering, and has an attractive, medium sized, glossy foliage.

I claim:

1. A new and distinct kalanchoe cultivar, substantially as herein shown and described, characterized by its abundant production of small bright pink florets which bloom on a plant of medium height and for an extended period due to several weeks of continuous flower bud developement.

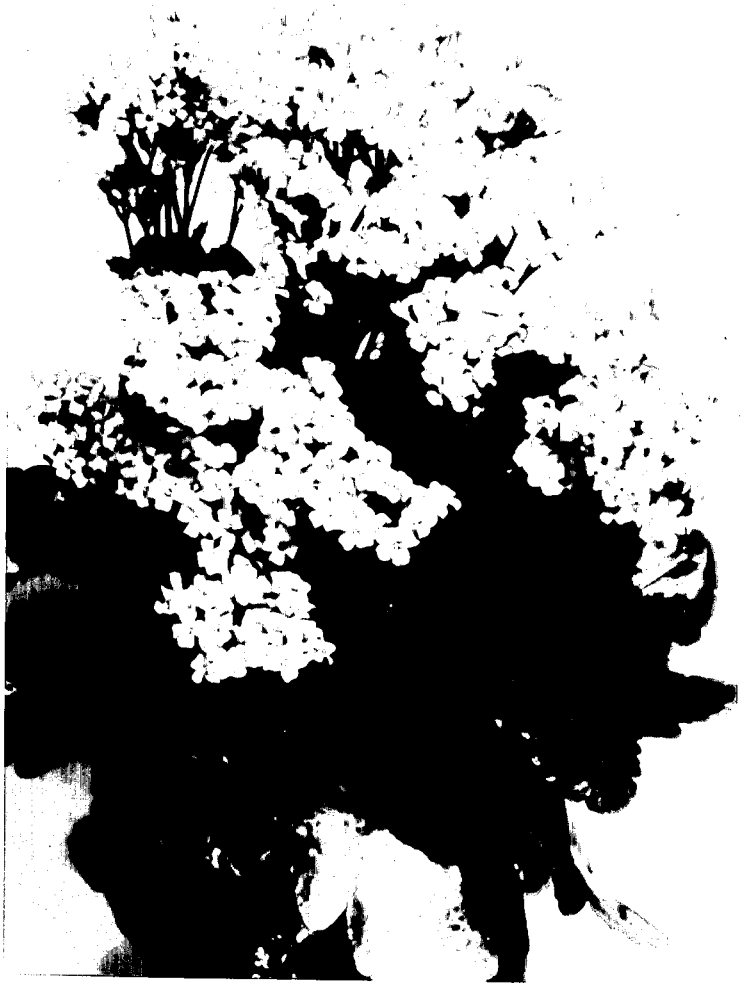

* * * * *